United States Patent [19]

Chen

[11] Patent Number: 5,370,776
[45] Date of Patent: Dec. 6, 1994

[54] ELECTROCHEMICAL IMPEDANCE SPECTROSCOPY METHOD FOR EVALUATING CORROSION INHIBITOR PERFORMANCE

[75] Inventor: Huey-Jyh Chen, Santa Ana, Calif.

[73] Assignee: Chevron Research and Technology Company, San Francisco, Calif.

[21] Appl. No.: 139,593

[22] Filed: Oct. 20, 1993

[51] Int. Cl.$^5$ ............................................. G01N 17/02
[52] U.S. Cl. .............................. 204/153.11; 204/404; 324/71.2; 324/425; 324/700
[58] Field of Search ................ 204/153.11, 404; 324/425, 71.2, 700

[56] References Cited

U.S. PATENT DOCUMENTS

| | | | |
|---|---|---|---|
| 4,095,176 | 6/1978 | Maes | 204/153.11 |
| 4,238,298 | 12/1980 | Tsuru et al. | 204/153.11 |
| 4,266,187 | 5/1981 | Slough | 204/153.11 |
| 4,658,365 | 4/1987 | Syrett et al. | 364/496 |
| 4,800,165 | 1/1989 | Oka et al. | 436/6 |
| 4,831,324 | 5/1989 | Asakura et al. | 324/615 |
| 4,881,037 | 11/1989 | Bellingham et al. | 324/425 |
| 5,006,786 | 4/1991 | McKubre et al. | 324/71.2 |

*Primary Examiner*—Aaron Weisstuch
*Attorney, Agent, or Firm*—M. W. Carson; W. K. Turner; D. J. Power

[57] ABSTRACT

A simple, expedient method for measuring the effectiveness of a corrosion inhibitor provided to a metallic surface by a surface layer, wherein the layer is formed by use of the corrosion inhibitor is a corrosive fluid. The method employs the measuring of a high frequency phase angle as an indicator of inhibitor effectiveness.

12 Claims, 7 Drawing Sheets

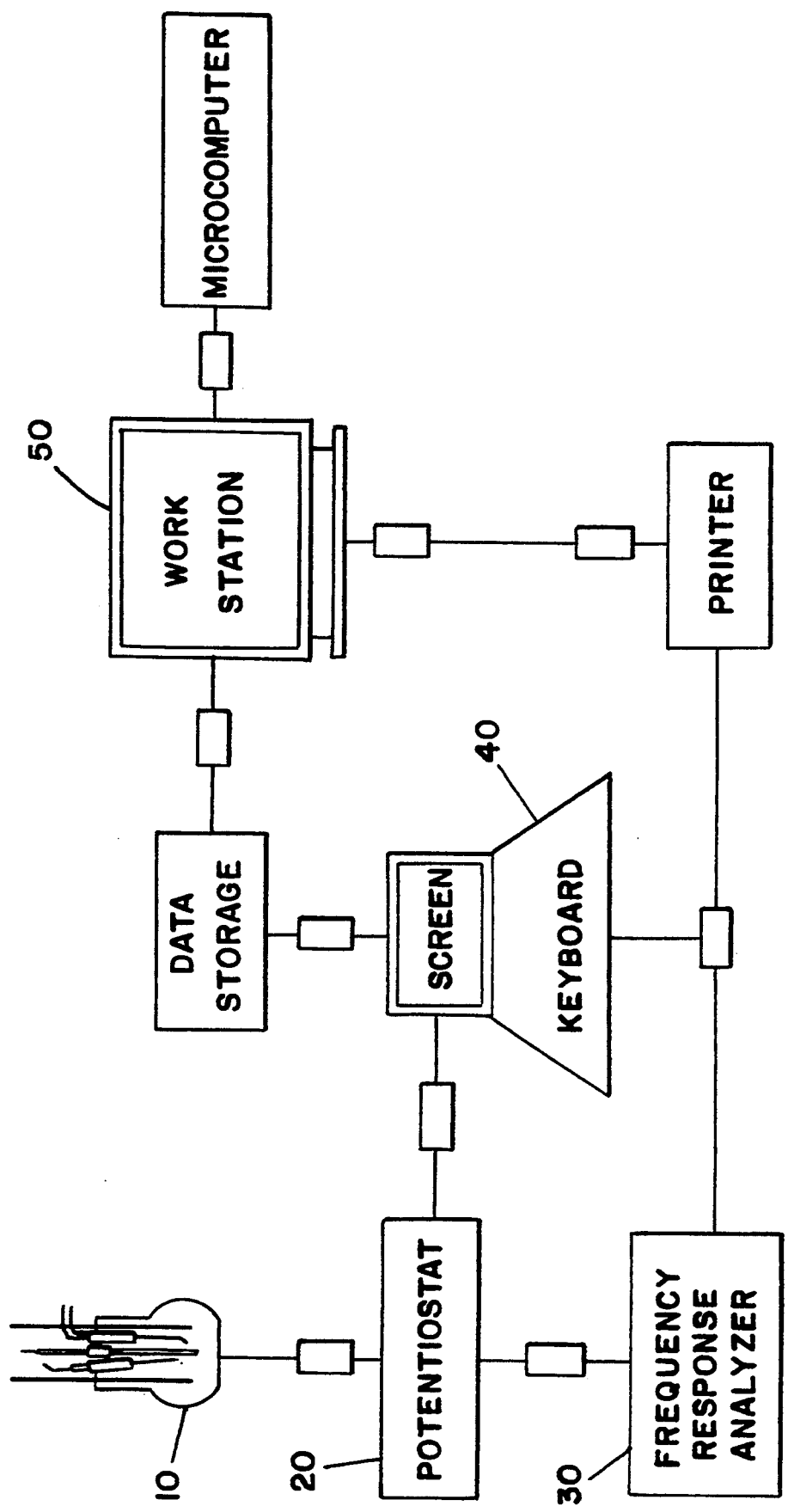
FIG_1

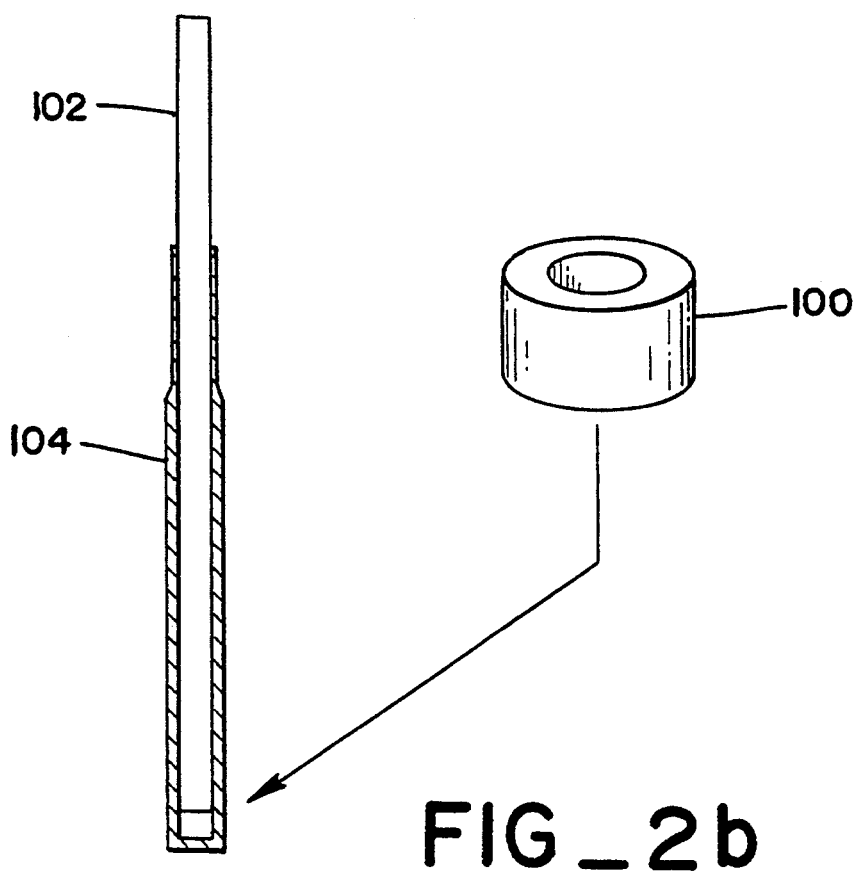
FIG_2b
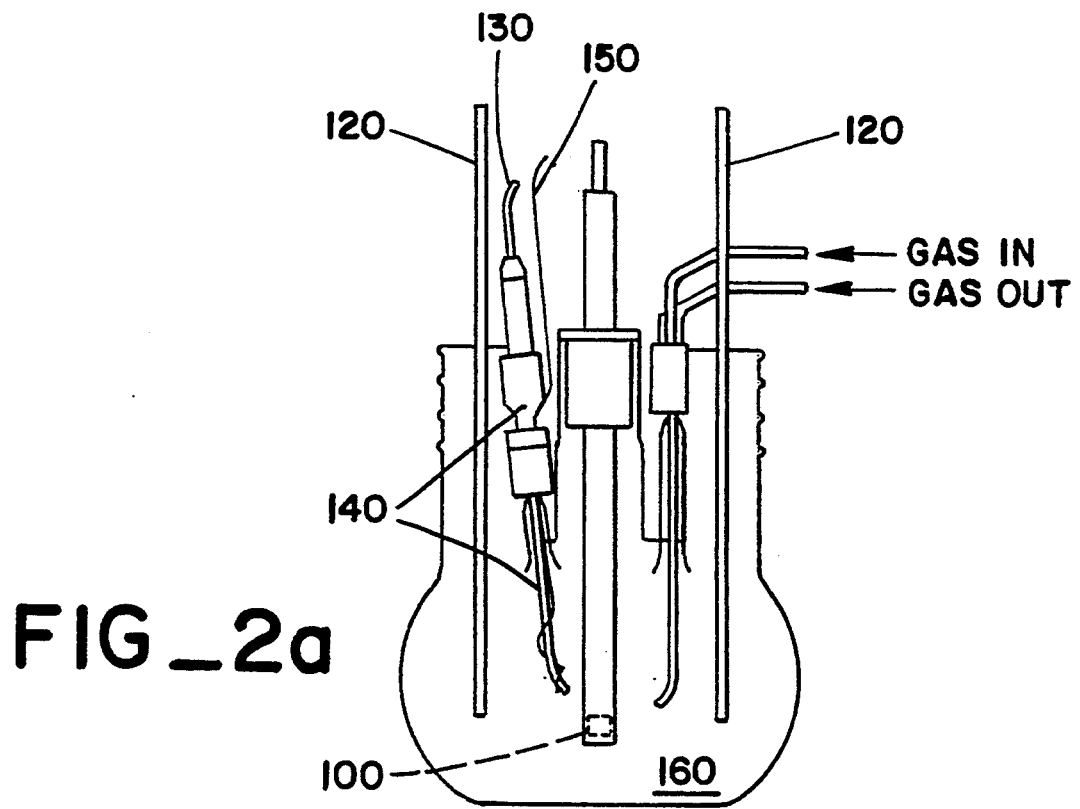
FIG_2a

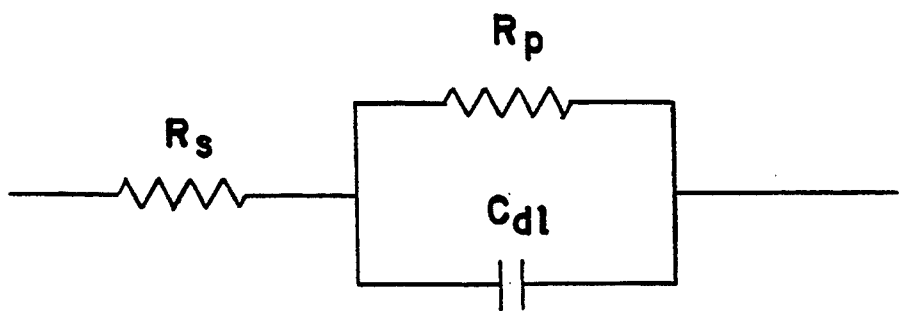
$R_s$ – SOLUTION RESISTANCE
$R_p$ – POLARIZATION RESISTANCE
$C_{dl}$ – DOUBLE LAYER CAPACITANCE
FIG_3
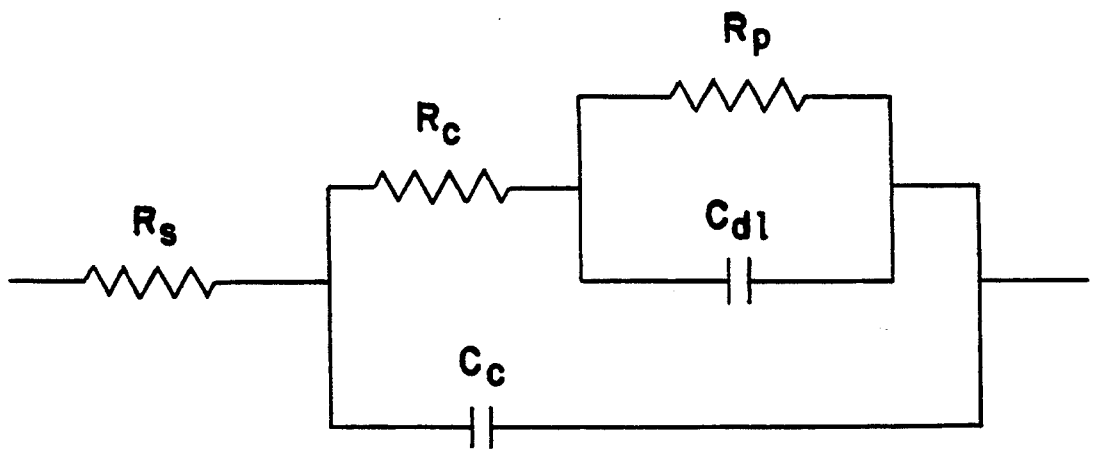
$R_s$ – SOLUTION RESISTANCE
$R_p$ – POLARIZATION RESISTANCE
$C_{dl}$ – DOUBLE LAYER CAPACITANCE
$R_c$ – COATING (INHIBITOR FILM) PORE RESISTANCE
$C_c$ – COATING (INHIBITED FILM) CAPACITANCE
FIG_4

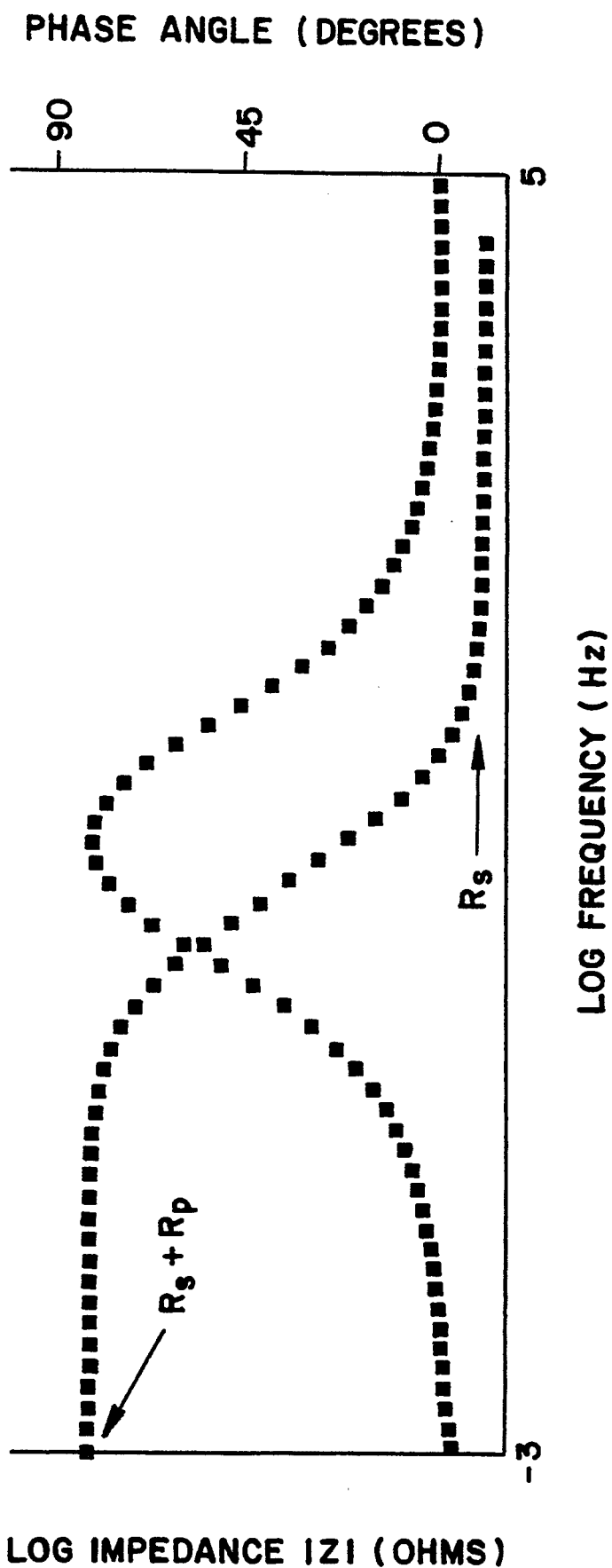

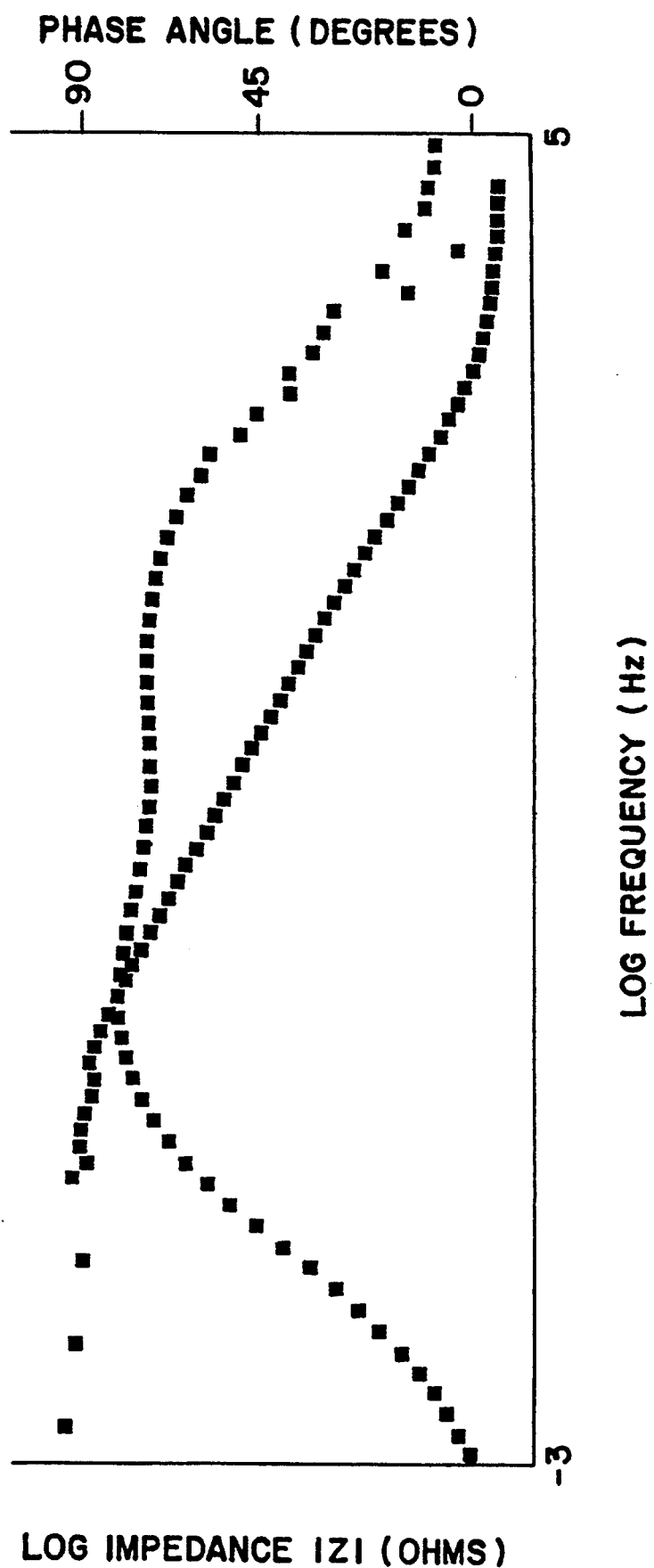
FIG_6

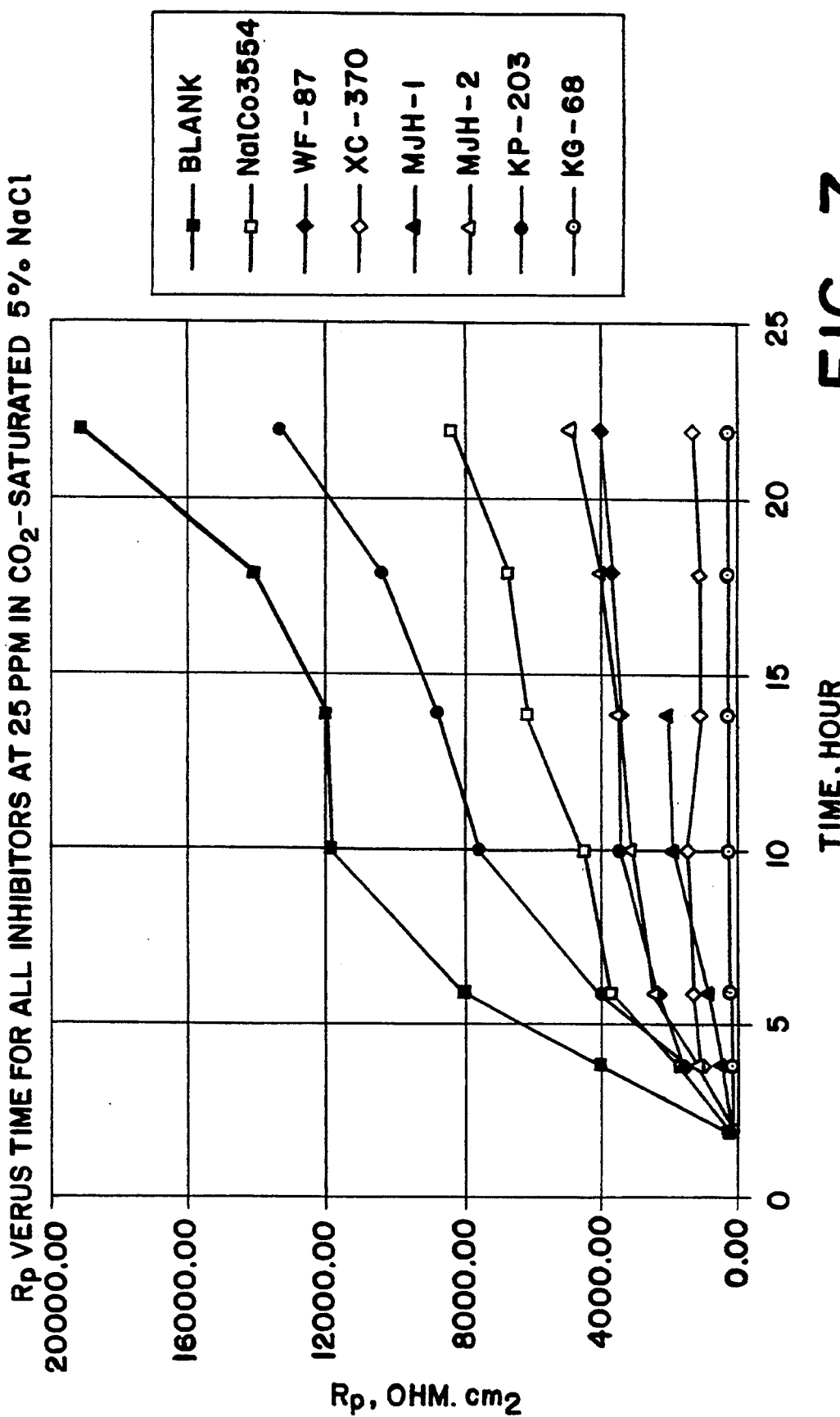

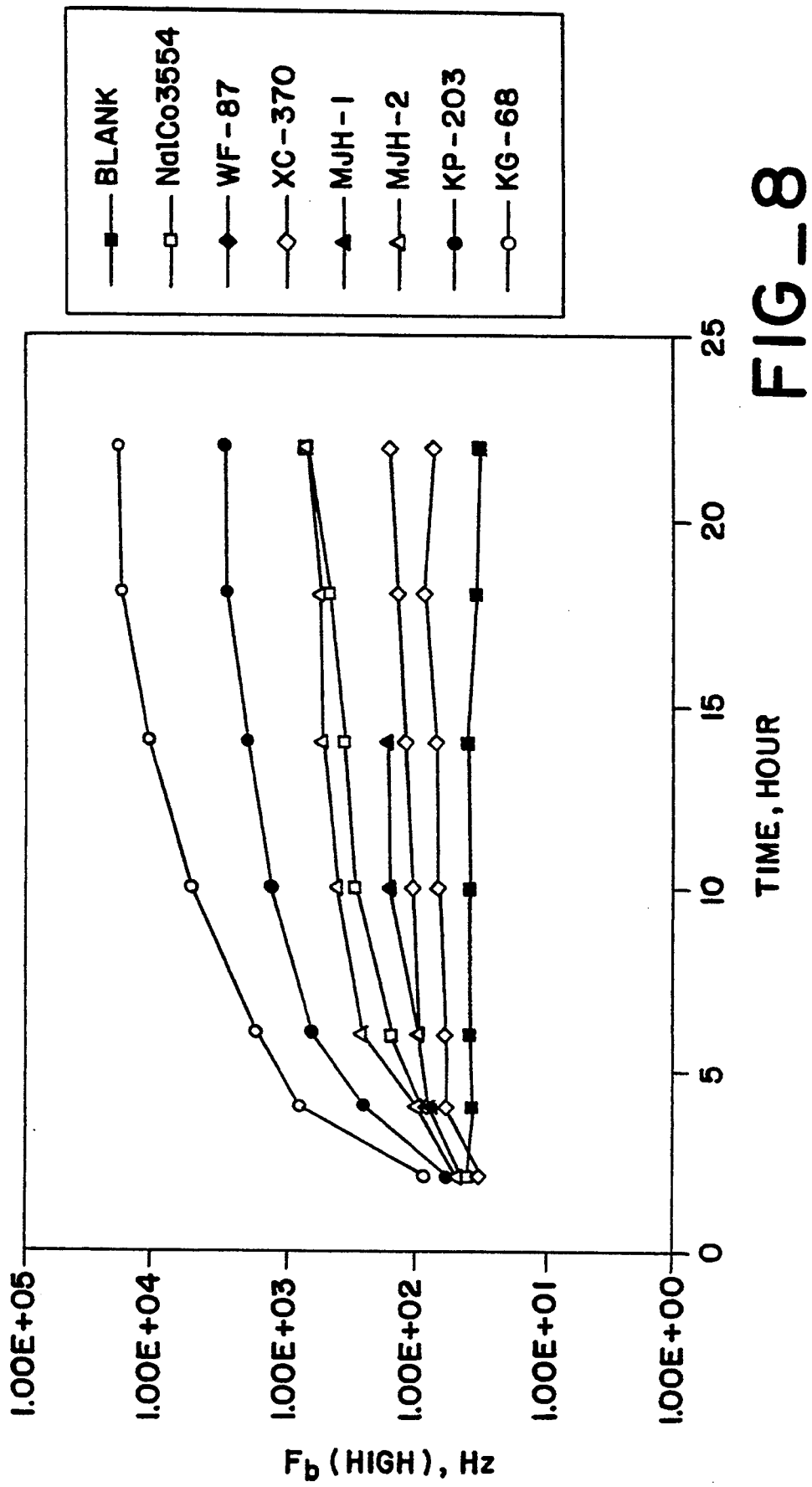

ELECTROCHEMICAL IMPEDANCE SPECTROSCOPY METHOD FOR EVALUATING CORROSION INHIBITOR PERFORMANCE

FIELD OF THE INVENTION

This invention relates to a method and apparatus for the evaluation of corrosion protection afforded by a corrosion inhibiting material. More specifically, it deals with an alternative measurement technique utilizing a high frequency at a varying phase angle as an indicator for monitoring inhibitor effectiveness.

DESCRIPTION OF THE PRIOR ART

Metallic surfaces are detrimentally affected by corrosive fluids in many fields of industry. For example, in the petroleum industry corrosion of metallic surfaces by petroleum materials occurs at all stages of production and distribution. To reduce this corrosion, inhibitors are often utilized as a control method, particularly in the oil and gas industry. There are various inhibitors which work in different ways, as well as various screening procedures used for the selection of inhibitors. Some inhibitors work by neutralizing active ions, others by reducing ion mobility and others by changing the ion transport numbers. In all cases the electrical conductivity of the corrosive fluid is altered, and various electrical parameters contributing to the overall corrosion mechanism will be affected. Accordingly, by using the corrosive fluid as an electrolyte in which two electrodes are immersed, and by measuring electrical characteristics of the electrolytic circuit, it is possible to derive an indication of the level of corrosion which continues to occur.

Until now, corrosion rates have been evaluated and monitored by measuring the polarization current, wherein a working electrode and a measuring electrode of a different metal are immersed in the corrosive fluid, and a D.C. voltage is applied across the two operative electrodes. By correlating potential difference increments, against current increments, a measure of the polarization current can be derived. Typically the use of linear polarization and potentiodynamic polarization are the D.C. methods used to determine corrosion rate.

In practice, however, the measurement of polarization current does not give a reliable evaluation of corrosion protection. Although the measurement may indicate very Little residual corrosion at the working electrode, the measurements taken a short distance away from the working electrode indicate that substantial corrosion may still be occurring. Other methods, based upon measured circuit characteristics such as solution resistivity and electrode capacitance, as well as polarization current, have been devised in an attempt to provide a more reliable evaluation technique for corrosion control. An example of a method utilizing electrode capacitance is disclosed in U.S. Pat. No. 4,095,176 to Maes et al., incorporated herein.

More recently, the use of electrochemical impedance spectroscopy (EIS) data has been developed as a new tool for conducting corrosion research. Using an equivalent electrical circuit comprised of a network of resistor, capacitor, inductor and constant phase elements, which are correlated to the physical and electrochemical properties of the system, allows the application of EIS data to various electrochemical properties, particularly corrosion and corrosion inhibition processes. In addition to mechanistic processes, EIS analysis can provide corrosion rate information, and has the advantage of allowing measurements to be conducted in low conductivity solutions where conventional D.C. techniques are subject to serious measurement error. This analysis is based upon the measurement of the polarization resistance of the system through the use of a low amplitude sinusoidal voltage in an extremely low frequency region, applied over a long period of time, and using this resistance measure to calculate the corrosion current density for the system.

This analysis, however, requires a significant amount of time to measure the polarization resistance, making it difficult for use in a field environment. It is therefore an object of the present invention to provide an expedient means for determining polarization resistance to allow for a timely and accurate measure of inhibition performance.

SUMMARY OF THE INVENTION

The present invention concerns a test method for evaluating the performance of a corrosion inhibitor utilizing the novel direct correlation method discovered to exist between the high "break point frequency", the frequency which occurs at 45° phase angle, and the corrosion rate for a given system. By the method of the present invention, the results of an EIS data analysis for a corrosive system are categorized into specific parameters; those related to the corrosion process such as polarization resistance ($R_p$) and double layer capacitance ($C_{dl}$), those related to inhibited film properties such as pore resistance ($R_c$) and film capacitance ($C_{-c}$) and those parameters related to the specific system being studied such as the maximum phase angle ($\theta_{max}$) frequency at maximum phase angle ($f_{\theta max}$), and the breakpoint frequency ($f_b$). These parameters can then be used to evaluate and rank the performance of various corrosion inhibitors introduced to the system. The present method recognizes that when a ranking based on the corrosion process parameter of polarization resistance ($R_p$) is compared to a ranking based on the system parameter of high breakpoint frequency ($f_b$), each ranking is identical. The present method exploits this correlation by measuring the high frequency at 45° phase angle of a corrosive system before and after the addition of a corrosion inhibitor, and measuring the inhibitor's effectiveness by comparison. Because of the excellent correlation, the higher the high frequency at 45° phase angle measurement in the inhibited system, the higher the polarization resistance and the lower the corrosion rate.

BRIEF DESCRIPTION OF THE DRAWINGS

FIG. 1 depicts the data acquisition and analysis system used in conducting EIS analysis.

FIG. 2a depicts the electrochemical cell used in the EIS measurement.

FIG. 2b is the electrode assembly used in the electrochemical cell of FIG. 2a.

FIG. 3 is a circuit model corresponding to a simple electrochemical corrosion cell.

FIG. 4 is a circuit model corresponding to a coated (or inhibited film) metal electrolyte system.

FIG. 5 is a Bode plot of impedance Z and phase angle $\theta$ as a function of frequency for a simple electrochemical corrosion cell.

FIG. 6 is a Bode plot of impedance Z and phase angle $\theta$ as a function of frequency for a coated metal system.

FIG. 7 is a plot of polarization resistance $R_p$ versus immersion time for inhibitors listed in Table 1.

FIG. 8 is a plot of high breakpoint frequency versus time for the inhibitors listed in Table 1.

DETAILED DESCRIPTION OF THE INVENTION

An important method for permitting the determination of inhibitor effectiveness in a corrosive system in an expedient manner is of particular value, particularly in the selection of inhibitors and the optimization of treating programs. By providing a method and/or system according to this invention, the monitoring of inhibitor effectiveness may be employed in the field environment to avoid over-treating a particular system with a particular inhibitor, as well as use as a tool to evaluate the overall corrosion processes.

In identifying the unique correlation between polarization resistance ($R_p$) and the frequency measurement at high frequency at 45° phase angle ($f_b$), EIS analysis was conducted utilizing the data acquisition and analysis system depicted in FIG. 1. As shown in FIG. 1 an electrochemical cell 10 is connected to an EG&G Model 273 potentiostat 20 and a Solartron Model 1255 frequency response analyzer 30; both of which are interfaced to an HP 9836S computer 40 and UNIX workstation 50 for data acquisition and analysis. EIS measurements were carried out at open circuit potential with an amplitude of 10 mv in the frequency range of about 5.5 mHz to about 55 KHz.

The electrochemical cell is shown in detail in FIG. 2a wherein cylindrical test coupons of C-1018 mild steel, having a total area of about 3.0 cm², are used as working electrode 100. The working electrodes are affixed to an electrode assembly shown in FIG. 2b, which comprises an isolated ¼" steel shaft 102 having a 12 mm Kel-F insulation jacket 104 on the lower portion subjected to the corrosive media of the cell. Referring again to the electrochemical cell of FIG. 2a, graphite counter electrodes 120 are shown in conjunction with a Saturated Calomel Electrode (SCE) acting as the reference electrode 130, which is connected to salt bridge 140. A platinum wire 150 is placed alongside the salt bridge and is coupled to the reference electrode through a 1.0 nf capacitor (not shown) to minimize the high frequency phase shift in the EIC measurements due to the slow response of the SCE. The corrosive media 160 used was approximately 900 ml of 5% NaCl brine which was deaerated with nitrogen and purged for 30 minutes with $CO_2$ to ensure $CO_2$ saturation of the brine. EIS measurements were conducted, utilizing the data acquisition and analysis set up at FIG. 1, two hours after the coupons were immersed and precorroded to establish the baseline data. An inhibitor of desired concentration was next injected into the cell, after which EIS measurements were again taken, followed by subsequent measurements every 2 to 4 hours. The EIS spectra obtained for the corrosion inhibitor evaluation were based upon the circuit models shown in FIGS. 3 and 4. FIG. 3 is an equivalent circuit corresponding to a simple electrochemical corrosion cell having a one time constant impedance spectrum, wherein $R_s$ is assigned as solution resistance, $R_p$ is the polarization resistance, and $C_{dl}$ is the double-layer capacitance between the metal and solution interface. FIG. 4 is the equivalent circuit for a coated or inhibited film-metal electrolyte system having a two-time constant impedance spectrum, wherein $R_c$ is assigned as the pore resistance of the inhibitor film, and $C_c$ is the capacitance of the coating or inhibitor film.

When conducting the EIS analysis, the first step is the determination of the polarization resistance, $R_p$. It is well known that the polarization resistance is related to corrosion rate by calculating the corrosion current density $I_{corr}$ according to the Stern-Geary equation:

$$I_{corr} = \frac{\beta_a * \beta_c}{2.303 \, (\beta_a + \beta_c) R_p} = \frac{k}{R_p} \quad (1)$$

where $\beta_a$ and $\beta_c$ are the anodic and cathodic Tafel constants, respectively, of the corrosion system, and K is a system constant related to the Tafel constraints. For the determination of $R_p$ in EIS, the potentiostat 20 of FIG. 1, develops a sinusoidal potential perturbation of very small amplitude, of about 10 mv, which is applied as a function of frequency. This slight excitation ensures that the measurement is performed in the linear region of the system, generally between about 100 kHz and 1 mHz. The impedance spectrum is then displayed as a Bode plot, displaying the impedance Z and phase angle $\theta$, each as a function of frequency f as shown in FIG. 5. The use of a Bode plot allows the capacitance (frequency-dependent) and resistance (frequency-independent) regions to be clearly distinguished; with the frequency dependence of the phase angle made apparent.

For a simple system with only one time constant impedance spectrum, as depicted in FIG. 5 and represented by the equivalent circuit of FIG. 3, polarization resistance, $R_p$, is determined by the difference between the impedance at a very high ($Z \rightarrow R_s$; $R_s$ is solution resistance) and a very low ($Z \rightarrow R_s + R_p$) frequency measured at corrosion potential. In a system having more than one time constant impedance spectrum, as depicted in FIG. 6 and represented by the equivalent circuit of FIG. 4, $R_p$ can be calculated by fitting the impedance data to the equivalent circuit of FIG. 4 using a nonlinear least-square fitting software program, such as LEVM, developed by J. R. MacDonald.

The effectiveness of a given corrosion inhibitor, in terms of percent protection, can be determined from the corrosion rate with or without the presence of a corrosion inhibitor. Since corrosion rate is inversely proportional to polarization resistance, the inhibition efficiency can be determined from the polarization resistance as shown in equation (2):

$$\% \text{ Protection} = \frac{R_{p(CI)} - R_{p(B)}}{R_{p(CI)}} * 100\% \quad (2)$$

where $R_{p(CI)}$ and $R_{p(B)}$ are polarization resistances with and without the presence of a corrosion inhibitor;respectively. Therefore, since polarization resistance, $R_p$, is related to corrosion rate as shown in equation (1); and assuming that the K value for the corrosive system is the same with or without the presence of an inhibitor, the corrosion inhibition of a particular inhibitor can be determined from equations (2).

FIG. 7 shows the plot of polarization resistance $R_p$ versus immersion time for the inhibitors listed in Table 1.

TABLE 1

| Chemistries of Inhibitors Studies | | |
|---|---|---|
| Inhibitors | Solubility | Description |
| Nalco3554 | water soluble | Fatty acid imidazoline, quaternary |

TABLE 1-continued

| Inhibitors | Solubility | Description |
|---|---|---|
| | | compound and arylsulfonic acid in alcohols |
| Petrolite WF-87 | water soluble | Fatty quaternary ammonium chloride in methanol, isopropanol and water |
| Petrolite XC-370 | water soluble | Oxydiethylene Bis(alkyl dimethyl ammonium chloride) in methanol and water |
| Chevron MJH-1 | water soluble | C-14 polyamine quaternized with benzyl chloride in isopropanol |
| Chevron MJH-2 | water soluble | MJH-1 plus nonyl phenol ethoxylate surfactant in isopropanol |
| Petrolite KP-203 | oil soluble | Cyclic aliphatic amine, oxyalkylated alkyphenols and a thiazole derivative |
| Petrolite KG-68 | oil soluble | Cyclic aliphatic amines, a highly sulfurized polyolefin and oxyalkylated alkylphenols |

The inhibitors were each studied at 25 ppm in the corrosive $CO_2$-saturated, 5% NaCl solution, and as evidenced in FIG. 7, each showed corrosion rates which decreased over time, indicating an increase in inhibitor effectiveness.

For each of the inhibitors studied there are two frequencies at 45° phase angle or "breakpoint frequency". The low breakpoint frequency occurs at a frequency lower than 13 Hz, and the high breakpoint frequency appears at a frequency higher than 30 Hz. A plot of high breakpoint frequency versus time for inhibitors in the corrosive solution is depicted in FIG. 8.

As shown in FIG. 8, high breakpoint frequency increases with increasing immersion time, with the order of increase the same as the corrosion rate profile for the inhibitors shown in FIG. 7. The higher the high breakpoint frequency, therefore, the higher the polarization resistance for the inhibitor and the lower the resulting corrosion rate. A comparison of FIGS. 7 and 8 verifies this direct correlation between, and identical ranking of, the high breakpoint frequency and the corrosion rate.

A mathematical correlation between polarization resistance, $R_p$, and breakpoint frequency, $f_b$, for a one time constant model as represented by the circuit of FIG. 3 and observed from the Bode plot of FIG. 5, is as follows:

$$Z_{tot} = R_S + R_p/\{1.0 + j\omega R_p C_{dl}\} \quad (3)$$

$$= R_S + R_p(1.0 - j\omega R_p C_{dl})/\{1.0 - (j\omega R_p C_{dl})^2\}$$

$$= R_S + R_p(1.0 - j\omega R_p C_{dl})/\{1.0 + (\omega R_p C_{dl})^2\}$$

$$= R_S + R_p/\{1.0 + (\omega R_p C_{dl})^2\} -$$
$$j\omega R_p^2 C_{dl}/\{1.0 + (\omega R_p C_{dl})^2\}$$

where
$Z_{tot}$ is the total impedance in ohm;
$R_s$ is solution resistance in ohm;
$R_p$ is polarization resistance in ohm;
$C_{dl}$ double layer capacitance in farad;
$\omega$ is angular frequency and equals $2\pi f$ rad/s;
f is the frequency in Hz and j equals $\sqrt{-1}$.

At frequencies of 45 degree phase angle, $f_b$, the following relations hold.

$$Z_{real} = |Z_{imag}| \quad (4)$$

$$|\text{Phase angle}| = 45° \quad (5)$$

and $$Z_{real} = R_s + R_p/\{1.0 + (\omega R_p C_{dl})^2\} \quad (6)$$

$$|Z_{imag}| = \omega R_p^2 C_{dl}/\{1.0 + (\omega R_p C_{dl})^2\} \quad (7)$$

Combining Equations (4), (5), (6) and (7), one has $$R_s + R_p/\{1.0+(\omega R_p C_{dl})^2\} = \omega R_p^2 C_{dl}/\{1.0+(\omega R_p C_{dl})^2\} \quad (8)$$

Case I—$R_s << R_p$
For $R_s << R_p$, we have $$R_s + R_p \approx R_p \quad (9)$$

Equation (8) becomes $$R_s R_p^2 C_{dl}^2 \omega^2 + R_p = \omega R_p^2 C_{dl} \quad (10)$$

and $$R_s R_p C_{dl}^2 \omega^2 - R_p C_{dl} \omega + 1.0 = 0 \quad (11)$$

Let $$\tau_1 = R_s C_{dl} \quad (12)$$

$$\tau_2 = R_p C_{dl} \quad (13)$$

Eqn. (11) becomes $$\tau_1 \tau_2 \omega^2 - \tau_2 \omega + 1.0 = 0 \quad (14)$$

The angular frequencies of 45 degree phase angle at high and low frequencies can be obtained by solving Eqn. (14) and the results are shown below:

$$\omega_b = \frac{\tau_2 \pm \text{sqrt}(\tau_2^2 - 4\tau_1\tau_2)}{2\tau_1\tau_2} \quad (15)$$

and $$\omega_b = \frac{1.0 \pm \text{sqrt}(1.0 - 4\tau_1/\tau_2)}{2\tau_1} \quad (16)$$

The frequencies of 45 degree phase angle, $f_b$, are obtained using Eqn. (17).

$$f_b = \frac{1.0 \pm \text{sqrt}(1.0 - 4\tau_1/\tau_2)}{4\pi\tau_1} \quad (17a)$$

or $$f_b = \frac{1.0 \pm \text{sqrt}(1.0 - 4R_s/R_p)}{4\pi R_s C_{dl}} \quad (17b)$$

It is obvious that both high and low frequencies at 45 degree phase angle are related with $R_s$, $C_{dl}$ and $R_p$. The increase of $R_p$ and the decrease of $C_{dl}$ move the high frequency at 45 degree phase angle to a higher frequency direction. Eqns. (17a) and (17b) are valid only at $R_s << R_p$. Since $R_s$ is an independent parameter which is determined by the conductivity of the electrolyte, therefore, a large $R_s$ value can be reduced by deconvolution. In this way, Eqn. (17) is also applicable to system with a low electric conductivity.

For a two-time constant model, represented by the equivalent circuit shown in FIG. 4, a mathematical correlation is derived as follows, where $R_s$ is solution resistance, $R_{po}$ is pore resistance, indicative of the conductive path of the coating, $R_p$ is the polarization resistance or coating resistance, $C_c$ is the coating capacitance and $C_{dl}$ is the double layer capacitance:

$$Z_{real} = R_s + R_{po}/(1+\omega^2\tau_2^2) + R_p(1-\omega^2\tau_2\tau_4)/\{(1+\omega^2\tau_2^2)(1+\omega^2\tau_4^2)\} \quad (18)$$

and $$|Z_{imag}| = \omega R_{po}\tau_2/(1+\omega^2\tau_2^2) + \omega R_p(\tau_2+\tau_4)/\{(1+\omega^2\tau_2^2)(1+\omega^2\tau_4^2)\} \quad (19)$$

with $$\tau_2 = R_{po}C_c$$

$$\tau_4 = R_pC_{dl}$$

At 45 degree phase angle, we have $$Z_{real} = |Z_{imag}| \quad (20)$$

The fourth-order equation of $\omega$ is shown as follows:

$$a'\omega^4 + b'\omega^3 + c'\omega^2 + d'\omega + e' = 0 \quad (21)$$

where $$a' = R_s\tau_2^2\tau_4^2;$$
$$b' = -R_{po}\tau_2\tau_4^2;$$
$$c' = R_s(\tau_2^2 + \tau_4^2) + R_{po}\tau_4^2 - R_p\tau_2\tau_4;$$
$$d' = -(R_{po}\tau_2 + R_p\tau_2 + R_p\tau_4);$$
$$e' = R_s + R_{po} + R_p.$$

By dividing $a'$ on both sides of Eqn. (21), Eqn. (22) can be used to get the four real roots if they are available.

$$\omega^4 b\omega^3 + c\omega^2 + d\omega + e = 0 \quad (22)$$

The four roots of $\omega$ are listed below:

$$\omega^2 + \{b+\sqrt{(8y+b^2-4c)}\}\omega/2 + \{y+(by-d)/\sqrt{(8y+b^2-4c)}\} = 0 \quad (23a)$$

$$\omega^2 + \{b-\sqrt{(8y+b^2-4c)}\}\omega/2 + \{y-(by-d)/\sqrt{(8y+b^2-4c)}\} = 0 \quad (23b)$$

and y is any real root of Eqn. (24).

$$8y^3 - 4cy^2 + (2bd-8e)y + e(4c-b^2) - d^2 = 0 \quad (24)$$

In order to solve Eqns. (22) to (24) for a real root, the following conditions are necessary.

$$R_{po} >> R_s;$$

$$R_p >> R_{po};$$

$$C_{dl} >> C_c;$$

The complete solution is time-consuming, however, if we consider Eqn. (22) without $R_s$ term (it is reasonable for polymer coating at $f_{b,1}$ occurs at very high frequency and $R_s << R_{po}$), we have $$a''\omega^3 + b''\omega^2 + c''\omega + d'' = 0 \quad (25)$$

with $$a'' = R_{po}\tau_2\tau_4^2;$$

$$b'' = -(R_{po}\tau_4^2 - R_p\tau_2\tau_4);$$

$$c'' = +(R_{po}\tau_2 + R_p\tau_2 + R_p\tau_4);$$

$$d'' = -(R_{po} + R_p).$$

Eqn. (25) can be solved by a standard methods well known, by using for example derivations provided by G. A. Korn and T. A. Korn in their reference text "Mathematical Handbook for Scientists and Engineers", McGraw-Hill, 1968.

According to the deviation in one-time constant model, the following method is provided as a solution for the two-time constant model:
Branch 1—elements $R_9$ and $C_c$;
Branch 2—elements $R_{po}$ and $C_c$;
Branch 3—elements $R_{po}$ and $C_{dl}$;
Branch 4—elements $R_p$ abd $C_{dl}$ The approximation of the $f_b$ at each branch is calculated as follows:

$$f_{b,1} = \{1+\sqrt{(1-4\tau_1/\tau_2)}\}/4\pi\tau_1 \quad (33a)$$

$$f_{b,1} = \{1+\sqrt{(1-4R_s/R_{po})}\}/4\pi R_sC_c \quad (33b)$$

$$f_{b,2} = \{1-\sqrt{(1-4\tau_1/\tau_2)}\}/4\pi\tau_1 \quad (33c)$$

$$f_{b,2} = \{1-\sqrt{(1-4R_s/R_{po})}\}/4\pi R_sC_c \quad (33d)$$

$$f_{b,3} = \{1+\sqrt{(1-4\tau_3/\tau_4)}\}/4\pi\tau_3 \quad (33e)$$

$$f_{b,3} = \{1+\sqrt{(1-4R_{po}/R_p)}\}/4\pi R_{po}C_{dl} \quad (33f)$$

$$f_{b,4} = \{1-\sqrt{(1-4\tau_3/\tau_4)}\}/4\pi\tau_3 \quad (33g)$$

$$f_{b,4} = \{1-\sqrt{(1-4R_{po}/R_p)}\}/4\pi R_{po}C_{dl} \quad (33h)$$

with
$$\tau_1 = R_sC_c;$$
$$\tau_3 = R_{po}C_{dl}.$$

The direct correlation of high breakpoint frequency and corrosion rate therefore allows for the evaluation of corrosion inhibitor performance by direct measurement of the high frequency at 45 degree phase angle. This method of evaluation is a great improvement and more expedient measurement of inhibitor performance than the determination of polarization resistance, which must be conducted at extremely low frequencies and can require as much as a ten fold increase in time to complete as compared to the present method. While the present method utilized the high breakpoint frequency, it will be recognized by those skilled in the art that other phase angles at high frequency, within a range of about 30° to 60° could also be used in conjunction with the method provided herein.

While particular embodiments of the present invention have been described above in considerable detail in accordance with the applicable statues, this is not to be taken as in any way limiting the invention by merely as being descriptive thereof.

What is claimed is:

1. A method of evaluating corrosion protection afforded to a metallic surface by a surface layer thereon, wherein said metallic surface is contacted by a corrosive fluid, said method comprising the steps of:
   establishing a circuit path through a working electrode and a reference electrode in the corrosive fluid;

causing a small sinusoidal potential perturbation at a high breakpoint frequency to flow in said circuit path;

measuring a reference high frequency at said high breakpoint frequency; and introducing a corrosion inhibitor to said corrosive fluid and measuring a response high frequency shift, said response high frequency being indicative of inhibitor efficiency.

2. The method according to claim 1 wherein the corrosion inhibitor is water soluble.

3. The method according to claim 1 wherein the corrosion inhibitor is oil soluble.

4. The method according to claim 1 wherein the sinusoidal potential perturbation has an amplitude of about 10 mV.

5. The method according to claim 4 wherein the frequency range of said perturbation is about 5.5 mHz to about 55 kHz.

6. The method according to claim 1 further comprising the step of correlating said response high frequency with a measured polarization resistance.

7. A method of evaluating corrosion protection afforded to a metallic surface by a surface layer thereon, wherein said metallic surface is subjected to a corrosive fluid having a corrosion inhibitor contained therein, said method comprising the steps of establishing a circuit path through a working electrode and a reference electrode in the corrosive fluid causing a small sinusoidal potential perturbation at a high-phase shifted frequency to flow in said circuit path measuring a high frequency response at said high-phase shifted frequency at differing time intervals to monitor changes in said high frequency response, said changes being indicative of changes in inhibitor efficiency.

8. The method according to claim 7 wherein the sinusoidal potential perturbation has an amplitude of about 10 mV and the frequency range of said perturbation is about 5.5 mHz to about 55 kHz.

9. The method according to claim 8 wherein the high-phase shifted frequency is a breakpoint frequency.

10. The method according to claim 7 wherein the inhibitor is water soluble.

11. The method according to claim 7 wherein the inhibitor is oil soluble.

12. The method of claim 7 wherein the frequency phase shift is between about 30° and 60°.

* * * * *